US009500468B2

United States Patent
Khomenko et al.

(10) Patent No.: US 9,500,468 B2
(45) Date of Patent: Nov. 22, 2016

(54) SCANNING INTERFEROMETRY TECHNIQUE FOR THROUGH-THICKNESS EVALUATION IN MULTI-LAYERED TRANSPARENT STRUCTURES

(71) Applicant: BOARD OF TRUSTEES OF MICHIGAN STATE UNIVERSITY, East Lansing, MI (US)

(72) Inventors: Anton S. Khomenko, Lansing, MI (US); Mahmoodul Haq, Lansing, MI (US); Gary L. Cloud, East Lansing, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 0 days.

(21) Appl. No.: 14/833,843

(22) Filed: Aug. 24, 2015

(65) Prior Publication Data
US 2016/0054116 A1 Feb. 25, 2016

Related U.S. Application Data

(60) Provisional application No. 62/041,415, filed on Aug. 25, 2014.

(51) Int. Cl.
*G01B 9/02* (2006.01)
*G01L 1/24* (2006.01)
*G01N 21/88* (2006.01)
*G01N 21/84* (2006.01)

(52) U.S. Cl.
CPC ............ *G01B 9/0209* (2013.01); *G01L 1/24* (2013.01); *G01N 21/8851* (2013.01); *G01N 2021/8438* (2013.01); *G01N 2021/8867* (2013.01)

(58) Field of Classification Search
CPC . G01B 9/0209; G01B 9/02091; G01L 1/241; G01L 1/24; G01N 21/8851; G01N 2021/8438
See application file for complete search history.

(56) References Cited

U.S. PATENT DOCUMENTS

| | | | |
|---|---|---|---|
| 4,072,423 A | 2/1978 | Kimura et al. | |
| 4,221,486 A | 9/1980 | Jaerisch et al. | |
| 4,322,162 A * | 3/1982 | McKelvie | G01L 1/24 356/35.5 |
| 4,325,637 A | 4/1982 | Moore | |
| 4,859,061 A | 8/1989 | Inoue | |
| 4,979,828 A | 12/1990 | Cronin-Golomb et al. | |
| 5,044,447 A | 9/1991 | Langeoire | |

(Continued)

FOREIGN PATENT DOCUMENTS

| WO | WO-01/94881 A1 | 12/2001 |
|---|---|---|
| WO | WO-2005/045403 A1 | 5/2005 |

OTHER PUBLICATIONS

Ai et al., Measurement of the inhomogeneity of a window, Opt. Eng., 30(9):1399-404 (1991).

*Primary Examiner* — Michael P Lapage
(74) *Attorney, Agent, or Firm* — Marshall, Gerstein & Borun LLP

(57) ABSTRACT

A multi-layer transparent composite detection technique includes producing two beams from a single, low-coherence source, a test beam and a reference beam, and scanning the reference beam to determine, with high precision, the depths of flaws (e.g., delaminations, bubbles, inclusions or other reflective or scattering objects) within a specimen or test object. The techniques combine light back-reflected or back-scattered from an internal flaw or interface with light in a reference path to identify such features and locations.

19 Claims, 13 Drawing Sheets

(56) References Cited

U.S. PATENT DOCUMENTS

| | | | |
|---|---|---|---|
| 5,173,744 A | 12/1992 | Dybwad | |
| 5,177,805 A | 1/1993 | Groger et al. | |
| 5,315,110 A | 5/1994 | Smith | |
| 5,327,219 A | 7/1994 | Steimle et al. | |
| 5,473,433 A | 12/1995 | Miller | |
| 5,488,477 A | 1/1996 | de Groot | |
| 5,568,256 A | 10/1996 | Korner et al. | |
| 5,694,217 A * | 12/1997 | Hizuka | G01B 11/161 356/491 |
| 5,754,714 A | 5/1998 | Suzuki et al. | |
| 5,923,425 A | 7/1999 | Dewa et al. | |
| 6,278,523 B1 | 8/2001 | Gorecki | |
| 6,285,956 B1 * | 9/2001 | Bennett | G01V 1/3808 367/16 |
| 6,304,362 B1 | 10/2001 | Zheludev et al. | |
| 6,359,678 B1 | 3/2002 | Ota | |
| 6,608,685 B2 | 8/2003 | Wood et al. | |
| 6,639,225 B2 | 10/2003 | Kirschstein et al. | |
| 6,639,682 B2 | 10/2003 | Neily et al. | |
| 6,657,731 B2 | 12/2003 | Tapalian et al. | |
| 6,665,077 B1 | 12/2003 | Stirniman et al. | |
| 6,668,111 B2 | 12/2003 | Tapalian et al. | |
| 6,687,423 B1 | 2/2004 | Yao | |
| 6,690,513 B2 | 2/2004 | Hulse et al. | |
| 6,727,992 B2 | 4/2004 | Hill | |
| 6,757,067 B2 | 6/2004 | Lee et al. | |
| 6,765,211 B2 | 7/2004 | Tapalian et al. | |
| 6,804,010 B1 | 10/2004 | Stirniman | |
| 6,806,963 B1 | 10/2004 | Walti et al. | |
| 6,898,221 B2 | 5/2005 | Berger et al. | |
| 6,903,354 B2 | 6/2005 | Goldstein | |
| 7,057,741 B1 | 6/2006 | Mueller et al. | |
| 7,120,334 B1 | 10/2006 | Greiner et al. | |
| 7,194,163 B2 | 3/2007 | Stepanov | |
| 7,196,011 B2 | 3/2007 | Cho et al. | |
| 7,260,281 B2 | 8/2007 | Salib et al. | |
| 7,289,224 B2 | 10/2007 | De Lega et al. | |
| 7,292,755 B1 | 11/2007 | Greiner et al. | |
| 7,302,183 B2 | 11/2007 | Sekine | |
| 7,375,825 B2 | 5/2008 | Ueki | |
| 7,399,096 B1 | 7/2008 | Lorell et al. | |
| 7,580,133 B2 | 8/2009 | Ueki et al. | |
| 7,697,796 B2 | 4/2010 | Kashyap et al. | |
| 7,723,015 B2 | 5/2010 | Miles | |
| 7,729,036 B2 | 6/2010 | Felnhofer et al. | |
| 7,751,527 B2 | 7/2010 | Ueda et al. | |
| 7,782,387 B2 | 8/2010 | Azuma | |
| 7,800,681 B2 | 9/2010 | Azuma | |
| 7,940,490 B2 | 5/2011 | Shelor | |
| 7,978,395 B2 | 7/2011 | Felnhofer et al. | |
| 8,111,446 B2 | 2/2012 | Gally et al. | |
| 8,242,446 B2 | 8/2012 | Fleury-Frenette et al. | |
| 8,427,652 B2 | 4/2013 | Bendix et al. | |
| 8,553,233 B2 | 10/2013 | Newman | |
| 8,582,088 B2 | 11/2013 | Bain et al. | |
| 2002/0176098 A1 | 11/2002 | Neily et al. | |
| 2003/0072009 A1 | 4/2003 | Domash et al. | |
| 2004/0160611 A1 | 8/2004 | Li | |
| 2004/0257586 A1 | 12/2004 | Jones | |
| 2005/0057757 A1 | 3/2005 | Colonna De Lega et al. | |
| 2005/0147921 A1 | 7/2005 | Lin et al. | |
| 2006/0126076 A1 | 6/2006 | Mueller et al. | |
| 2006/0198580 A1 | 9/2006 | Seguin et al. | |
| 2008/0278729 A1 | 11/2008 | Kim | |
| 2009/0018436 A1 | 1/2009 | Gey Van Pittius et al. | |
| 2010/0002739 A1 | 1/2010 | Hu et al. | |
| 2011/0134414 A1 * | 6/2011 | Jeannot | G01B 11/0625 356/72 |
| 2012/0172910 A1 * | 7/2012 | Forster | A61B 5/6853 606/194 |
| 2012/0176623 A1 * | 7/2012 | Lee | G01B 11/0675 356/503 |
| 2013/0128264 A1 * | 5/2013 | Wax | G01B 9/02044 356/300 |
| 2013/0335732 A1 | 12/2013 | Stewart | |
| 2014/0027708 A1 | 1/2014 | Goyal et al. | |
| 2014/0072770 A1 | 3/2014 | Hwang et al. | |
| 2014/0085317 A1 | 3/2014 | Lavery et al. | |
| 2014/0165236 A1 | 6/2014 | Budach et al. | |
| 2014/0166485 A1 | 6/2014 | Sailor et al. | |
| 2014/0168637 A1 | 6/2014 | Wan et al. | |
| 2014/0233016 A1 * | 8/2014 | Aiyer | G01B 11/2441 356/51 |
| 2014/0268174 A1 | 9/2014 | Sabry et al. | |
| 2015/0301268 A1 | 10/2015 | Bita et al. | |

* cited by examiner

SCANNING INTERFEROMETRY TECHNIQUE FOR THROUGH-THICKNESS EVALUATION IN MULTI-LAYERED TRANSPARENT STRUCTURES

CROSS-REFERENCE TO RELATED APPLICATIONS

This application claims the priority benefit under 35 U.S.C. §119(e) of U.S. Provisional Patent Application No. 62/041,415, filed Aug. 25, 2014, the disclosure of which is incorporated herein by reference in its entirety.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Multi-layered transparent composites having glass laminates with polymer interlayers and backing sheets are commonly used in a wide range of applications, where visibility, transparency, impact resistance, and safety are essential. These applications include, e.g., windshields on defense vehicles and armored vehicles, windshields on aircraft, and security enclosures in buildings, personal protection equipment, etc. Although multi-layered transparent composites and fiber reinforced plastics (FRPs) are conventionally considered to fall into the same class of materials, which is "composites," structurally they are significantly different. Owing to the differences of these structures, their defects are also different. While considerable literature on the development, manufacturing and optimization of these multi-layer transparent composites exists, information on nondestructive evaluation (NDE) and damage detection in these composites is very limited. The result is that determining defects and damage in multi-layer structures is very difficult. For example, identifying defects that result from manufacturing issues can be nearly impossible to detect, e.g., identifying which layer resulted in the defect. This can be particularly problematic as many defects are not discernible until after the entire multi-layered transparent composite assembly has been completed, sometimes after the composite has already been deployed into use. Moreover, during use, these multi-layered transparent composites are subjected to extreme environmental conditions in addition to their normal mechanical loads, which can lead to delamination and other losses that compromise structural integrity as well as transparency of the composite.

Hence, there is a considerable need for an efficient NDE technique that can provide detailed characterization of defects/damage and in all 3-dimensions of a thick layered structure. Current Conventional techniques can only provide, at best, an estimate of the 2D (XY, in-plane) location of the defect, and optical coherence tomography (OCT) is not quite suitable for evaluation of thick multi-layered transparent composites due to important issues of beam coincidence. And none of the conventional techniques are able to provide depth (Z-axis, through thickness) information about the damage in relatively thick multi-layered transparent composites.

SUMMARY OF THE INVENTION

Described herein are techniques for using interference between two beams from a single, low-coherence source to determine, with high precision, the depths of flaws (e.g., delaminations, bubbles, inclusions or other reflective or scattering objects) within a specimen or test object. The techniques can determine these flaws along any two dimensional area and at any depth of the material. The techniques combine light back-reflected or back-scattered from an internal flaw or interface with light in a reference path. By using light of low temporal coherence (e.g., a coherence on the order of a few to several tens of micrometers), interference will occur only when the beams are coincident and the object path and the reference path match within the coherence length of the light source. By changing the reference optical path length until interference occurs, a change of an object optical path length is established. By adjusting that reference optical path length by known increments, the locations of flaws within the specimen are determined. The locations of internal reflective or scattering sources relative to the specimen surfaces can be found.

In accordance to an example, a method of scanning a multi-layered specimen, the method comprises: receiving a coherent radiation beam and separating the coherent radiation beam into an object beam and a reference beam, the object beam and the reference beam being coherent with one another; directing the object beam at the specimen and collecting a resulting sampled beam from the specimen, wherein the sampled beam comprises reflected radiation from the specimen and/or backscattered radiation from the specimen; maintaining the reference beam along a reference beam path and free from incidence on the specimen, and scanning the reference beam along different optical path lengths of the reference beam path, wherein the scanning of the reference beam is along a reference axis coinciding with an axis into the specimen and over a depth region into the specimen; and combining the sampled beam with the reference beam to produce an interferometric intensity signal or pattern, where, as a result of the scanning of the reference beam, the interferometric pattern contains amplitude peaks that are caused by reflection or scattering from discontinuities at different depths within the depth region of the specimen.

In accordance with another example, an apparatus for scanning a multi-layered specimen, the apparatus comprises: a beam splitter positioned to receive a coherent radiation beam and configured to separate the coherent radiation beam into an object beam and a reference beam, the object beam and the reference beam being coherent with one another; a specimen scanning stage configured to direct the object beam at the specimen and collect a resulting sampled beam from the specimen, wherein the sampled beam comprises reflected radiation from the specimen and/or backscattered radiation from the specimen; a reference beam stage configured (i) to maintain the reference beam along a reference beam path and free from incidence on the specimen and (ii) to scanning the reference beam along different optical path lengths of the reference beam path, wherein the scanning of the reference beam is along a reference axis coinciding with an axis into the specimen and over a depth region into the specimen; and a signal analysis stage configured (i) to combine the sampled beam with the reference beam and produce an interferometric pattern, where, as a result of the scanning of the reference beam, the interferometric pattern contains amplitude peaks corresponding to discontinuities at different depths within the depth region of the specimen, and (ii) to analyze the interferometric pattern to identify discontinuities in the specimen from the peaks in the interferometric pattern.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Figure 1:
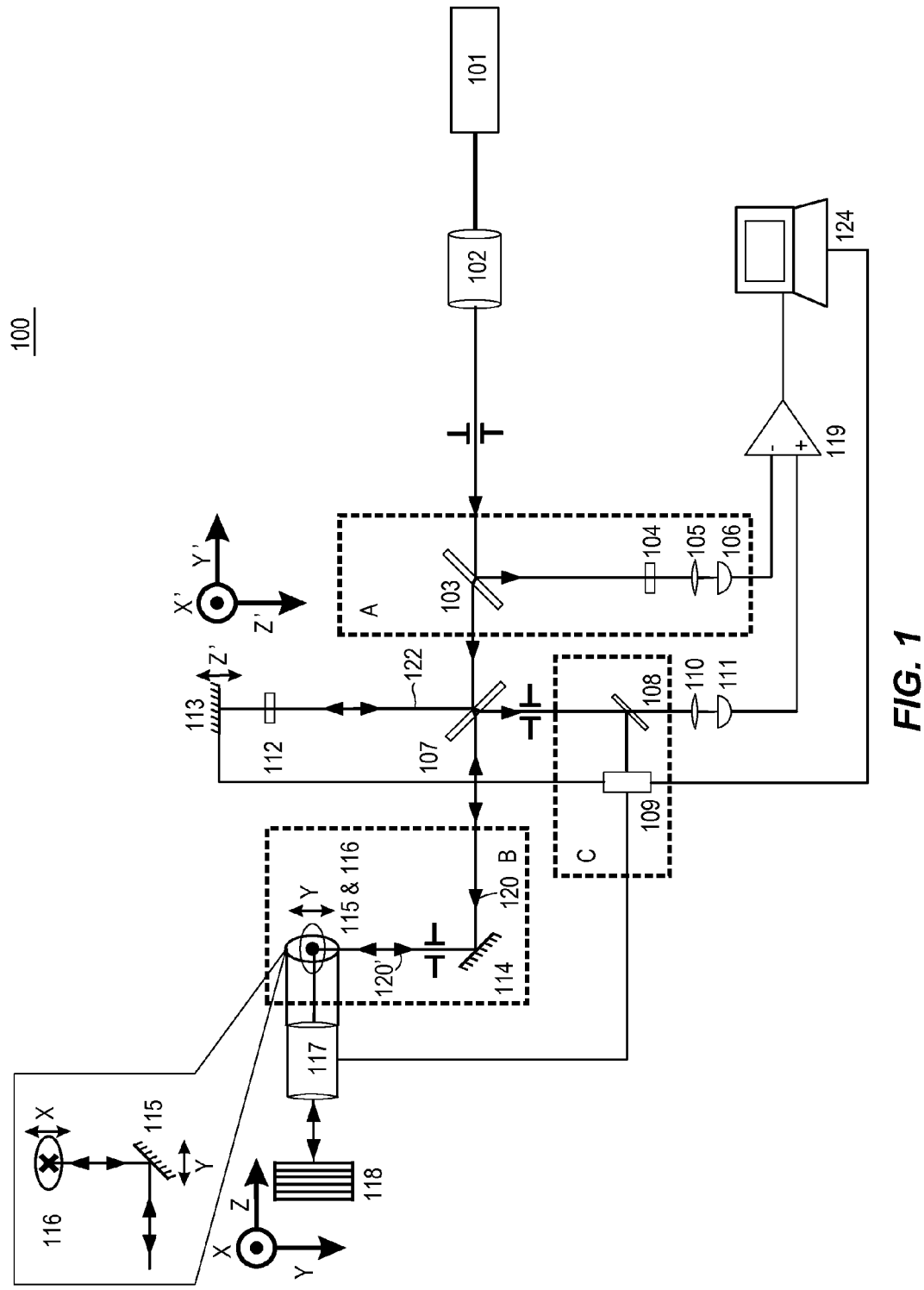
FIG. 1 illustrates a multi-layer transparent composite detection system, in accordance with an example.

The techniques disclosed herein use the radiation of a broad-spectrum light source. They are capable of non-invasive, non-contact, and real-time defect depth location identification. The techniques are capable of determining the size of such defects, with high spatial resolution obtained by scanning along the Z-axis direction. Moreover, that Z-axis scanning may be achieved by scanning through a precisely known range a test (object) beam, i.e., the beam incident upon a specimen, or that Z-axis scanning may be achieved by similarly scanning a reference beam of the interferometer. This latter configuration can allow for better control of defect detection, providing greater scanning flexibility by separating the XY-axis (in plane) scanning from the Z-axis (depth) scanning. Moreover, while both Z-axis scanning techniques allow for dual course and fine Z-axis scanning, using a non-contacting reference beam for Z-axis scanning can allow for better control of and transition over the switching points between coarse and fine measurements. This combination of coarse scanning and fine scanning allows for faster scanning through a layer where defects are less likely and smaller incremental (and more accurate) scanning at regions near surface boundaries for those layers.

In any event, the present techniques are capable of providing information that completely characterizes damage to a multi-layer transparent composite, in terms of location and size. Moreover, these techniques may be implemented in the field, i.e., on composites that have already been installed for use. In some examples, the techniques are used for detecting the onset of defects and for measuring growth of defects over time. That growth can be determined over a three-dimensional region within the specimen, due to the XY-plane scanning and Z-axis scanning. Some defects are not confined to a particular plane or even a particular layer of material in a multi-layer transparent composite. Delamination, for example, creates an air gap between layers; and that air gap can grow over time, creating a defect that extends in both in-plane and Z-axis directions. The full three-dimensional scanning of the present techniques allows for tracking and identifying the sizes of defects as they grow inside a specimen.

In some examples, embedded signal-to-noise ratio (SNR) enhancement is used to substantially increase sensitivity to defect detection. The present techniques can detect defect positions at resolutions (along the Z-axis) commensurate with the size of the smallest layers in multi-layer transparent composite structures (e.g., a few to hundreds of micrometers, e.g., 1 micrometer to 1 millimeter). The high SNR also allows for defect detection in relatively high-absorption and high-scattering composites. Furthermore, with the high sensitivity levels achievable, different defects can be detected at different depths, even when those defects overlap in terms of XY-plane position. By using temporal coherence interferometry, reflected radiation and /or backscattering from different depths are detectable with the present system, thereby allowing for depth differentiation and isolation of defects at different stratifications, even with other defects overlapping at higher or lower stratifications.

FIG. 1 illustrates an example of such a multi-layer transparent composite detection system 100. The system 100 is, generally speaking, in an amplitude splitting interferometry configuration, but one that uniquely utilizes a low-coherence light source, a two (2) step long range reference mirror stage and a beam tracking, control, and alignment module.

In the illustrated example, light source 101 is a laser light source having a relatively low temporal coherence. Temporal coherence is defined as the property of the light source in which the electromagnetic waves maintain a fixed and predictable phase relationship with each other over a period of time. The delay over which the phase or amplitude wanders by a significant amount is defined as the coherence time $\tau_c$. The coherence length $L_c$ is defined as the distance the wave travels in time $\tau_c$ and is given by the following equation $$L_c \approx \frac{\lambda^2}{\Delta\lambda},$$

where $\lambda$ and $\Delta\lambda$ are the central wavelength and the spectral width of the source respectively. Typical values of coherence length for low-coherent light sources vary from a few micrometers to several millimeters.

Generally speaking, the light source 101 may be a laser light source, such as a semiconductor laser, solid-state laser, gas laser, fiber-based laser, dye laser, diode laser, photonic crystal laser, etc. In other examples, the light source is a non-lasing, broad spectrum radiation source, but one that produces radiation with a sufficient, partial coherence to be used for interferometry detection. In some examples, the coherence of the output radiation (laser or non-lasing) may be achieved by altering the coherence of the radiation after exiting the light source 101, for example by using an external cavity. In any event, the light source 101 may produce a continuous radiation output or a pulsed radiation output.

The output radiation from the light source 101 is coupled to an optical telescope 102, which controls beam width and divergence, e.g., collimating the radiation for progression through the system 100.

The radiation from the telescope 102 is divided into two beams by a main beamsplitter 107. The radiation transmitted through main beamsplitter 107 forms an object (or test) beam 120; and the light reflected by main beamsplitter 107 forms a reference beam 122. A specimen 118 under examination is positioned downstream to receive the object beam 120, which is able to scan the specimen 118. That is, unlike the reference beam 122, the object beam 120 directly impinges upon on the specimen 118. In the illustrated example, the specimen 118 is a multi-layer transparent composite, where at least some of the layers are formed of different materials and/or at different thicknesses. It will be appreciated that in other examples, the specimen 118 may be formed of a homogenous material throughout. The detection of reflected radiation or backscattered radiation will be detectable in homogenous structures, as well.

In some examples, the specimen 118 is mounted on a translation stage for movement in an XY-plane, in order to provide 2D in-plane scanning. For specimens that cannot be separately scanned, the system 100 uses a specimen scanning stage identified as assembly B in FIG. 1. The object beam 120 is reflected by a mirror 114, which reflects the beam 120 to a mirror 115 that can be translated horizontally, along the y-axis. The mirror 115 reflects the beam vertically (see exploded view) to a mirror 116 that can be translated along a vertical direction, along the X-axis. Therefore assembly B is able to perform XY-plane scanning (in-plane) of the specimen 118, which may be stationary or moving.

The object beam 120 is focused onto the specimen 118 (transparent multi-layered structure) through use of a Z-axis adjustable optical telescope 117. It is known that the change of the refractive index at the structure interface(s) causes a portion of the radiation to be reflected back. Since an adjustable optical telescope 117 is used, it is possible to get not only back-reflected radiation but also back-scattered radiation from the exterior surfaces and regions within the specimen, in particular from surfaces of the multiple layers forming the composite and defect interfaces.

As the object beam 120 is incident and enters the specimen 118, there may be several reflected or scattered beams, all more or less coincident, and each having undergone its own unique optical path length modification as it exits the specimen 118, through the front face nearest the telescope 117. The system 100 is able to separate and measure these individual optical path length differences, i.e., from different surfaces, surface transitions, and/or defects, so as to identify their depths within the specimen 118. By interrogating the combination of returning radiation (beams), the system 100 is able to identify and measure various characteristics of the returning beams in order to, in turn, characterize the reflectors and scatterers within the specimen 118, including their XY-plane location, Z-axis location, and respective sizes in three dimensions.

The system 100 discerns Z-axis location of a surface, a surface transition, or a defect through an interference between the returning object beam 120' and the reference beam 122. The use of a low-coherence radiation source 101 allows for precision across any depth within the specimen 118. Interference between one of the returning object beams 120' and the reference beam 122 will occur only when their optical path lengths match to within the coherence length of the light source 101. If the reference beam optical path length is changed by a precisely known amount until interference occurs, then the change of reference beam optical path length matches exactly the optical path length difference that has occurred in one of the returning object beams. If this process is continued through the full range of optical path length differences, then the optical path length changes for all returning beam components can be determined, among which will be the reflections from various front and back surfaces of the layers forming the multi-layer structure of the specimen 118 as well as its internal defects and interfaces. That is, all the internal sources of reflection or scattering, whether defects or composite layers, can be precisely located with respect to specimen coordinates using the adjustment of the reference beam 122 and interference.

To affect adjustment to the reference beam optical path length, a reference mirror 113 is used that is capable of being moved by precise, known amounts. That movement, as shown, reflects movement along a Z-axis (labeled as Z'-axis) as defined relative to the specimen 118. That is, the orthogonal coordinate orientation of the reference mirror 113 looks different from that of the stage B, but in fact, the movement of the mirror 113 coincides with movement along the Z-axis of the stage B.

The mirror 113 is adjustable in both course and fine known movements, in some examples. Course movements may be used, for example, when scanning through the thickness of a layer, until the front or back of that layer is reached, where a subsequent layer is attached. At a transition from a back layer to a front layer, for example, the mirror 113 may be controlled to have a fine adjustment given that the reflected radiation or backscattering will occur over a smaller region on the order of the coherence length of the light source. The fine adjustment is more useful for identifying defects and determining characteristics of defects, once identified. In other words, the reference mirror 113 may be translated using a 2-step long-range stage providing both coarse long-range and very precise local translations.

The mirror 113 may be oscillated at a relatively high frequency (i.e. from a few to several kHz, e.g., 1 kHz to 20 kHz) in the Z'-axis with amplitude up to several coherence lengths of the light source (i.e. a few micrometers to several millimeters, e.g., 1 micrometer to 3 millimeters), in order to create an alternating current (AC) interference intensity signal that can be processed. That is, the reference beam 122 reflected from the main beamsplitter 107 is attenuated by a filter 112 and may be reflected back by the modulating reference mirror 113. Modulation of the reference mirror 113 can be achieved by using harmonically oscillating actuators, i.e., a lead zirconium titanate (PZT) structure, magnetostrictive, electromagnetic, mechanical, etc. Whether modulating or not, the precise range of translation of the reference mirror 113 along the Z-axis (Z"-axis) should be equal to or exceed the depth to which the test object 118 is to be scanned.

The reflected or scattered object beam 120' and the reference beam 122 are reflected back to the main beamsplitter 107. In the illustrated example, a small portion of the collective radiation is reflected by a beamsplitter 108 to a monitoring device 109, which may be a charge-coupled device (CCD) sensor, complementary metal-oxide-semiconductor (CMOS) sensor, screen, or other photodetector.

The monitoring device 109 has one or more detectors coupled to active feedback devices (e.g., servo motors on the mirror 113 and on the objective 117) to control the adjustable optical telescope 117 and adjust the angle Z-of the reference mirror 113. The monitoring device 109 is used as a part of a feedback control that may be used to control object beam divergence as well as the position of the reference beam 122 required to bring the object beam 120' and the reference beam 122 into coincidence so that they can interfere. This beam coincidence adjustment may be particularly useful given the low intensity levels that can result from different reflected and scattered beams. Angles of reflection or scattering as well as beam intensities can vary with depth in the specimen 118 and from the size of the originating defect or surface. Moreover, constructive interference occurs only when the object beam 120' and the reference beam 122 are coincident and their paths are equal within the span of the coherence length of the laser source. Thus, the beamsplitter 108 and the monitoring device with active feedback 109 form a beam tracking and alignment stage C, operating as a beam tracking, control and alignment module for the system 100.

It will be appreciated that, as with the other stages described herein, the beam tracking and alignment stage may be implemented with other elements that are able to combine a sampled beam with a reference beam or perform other actions for beam tracking, control, and alignment.

Moreover, it will be appreciated that any of the systems described may be implemented with single coherent beam or multiple coherent beam configurations. For example, an incident laser radiation beam may represent multiple incident laser beams, each different in wavelength, polarization orientation, etc. In such examples, multiple object and reference beams would propagate through a system for analysis, where each of the stages affect the multiple beams as described herein. In any event, it will be appreciated that references herein to a single radiation beam, object beam, reference beam, sampled beam, etc. are meant to also include references to a plurality of radiation beams, a plurality of object beams, a plurality of reference beams, a plurality of reference beams, a plurality of sampled beams, respectively. The systems may then produce a plurality of corresponding interferometric intensity signals or patterns that can be analyzed, for example, interferometric intensity signals or patterns that are each at a different beam center wavelength.

The radiation returning from the specimen 118 (beam 120') is partially diverted by the main beamsplitter 107. The majority of diverted radiation is not reflected by the beamsplitter 108, but rather passes through and is focused by a lens 110 onto a photodetector 111.

In order to reduce laser noise effects and increase signal-noise ratio (SNR), the system 100 includes a balanced photodetector stage A. After the initial beam from the light source 101 exits the optical telescope 102, a portion of the beam (a signal balancing beam) partially reflects from a reference beamsplitter 103 and is focused by a lens 105 onto the reference photodetector 106. The reference photodetector 106 may be balanced with a tunable filter 104, for example, a polarizer that adjusts the intensity of the beam incident on the photodetector 106. The stage A, thus, addresses situations where low intensity signal level from the specimen 118 exists and/or where there are relatively high amounts of absorption or scattering.

The output from the photodetector 111 is coupled to an optional amplifier 119 coupled to a signal processing machine 124. That is, in the illustrated example, the beamsplitter 108, lens 110, photodetector 111, amplifier 119, and signal processing machine 124 form a signal analysis stage.

The amplifier 119 is used to increase the level of the photodetector signal, if needed. In the illustrated example, the amplifier 119 is a differential amplifier, which is used in balanced photodetector configurations. Because it is a differential amplifier, it serves to cancel or reduce intensity noise that is inherent in radiation from almost all sources.

The signal processing machine 124 (e.g., an oscilloscope, data acquisition card, personal computer, server, or other processing device) is coupled to the photodetector 119 and records the interference signal data, including the intensity data. The machine 124 analyzes the recording signal data from the amplifier 119. The machine 124 may also be coupled to the scanning stages for the reference mirror 113, the test mirrors 115 and 116, and the objective 117, to collect position data for these mirrors and convert that physical position data to an XY-plane coordinate and Z-axis coordinate of the data for determining and displaying surface position and defect position and size. That is, in this way, the scanning with reference mirror 113 in a 2-step scanning stage (course and fine) allows precise determination of the locations of all the interfaces, defects, and other scattering regions in the specimen 118.

Figure 2:
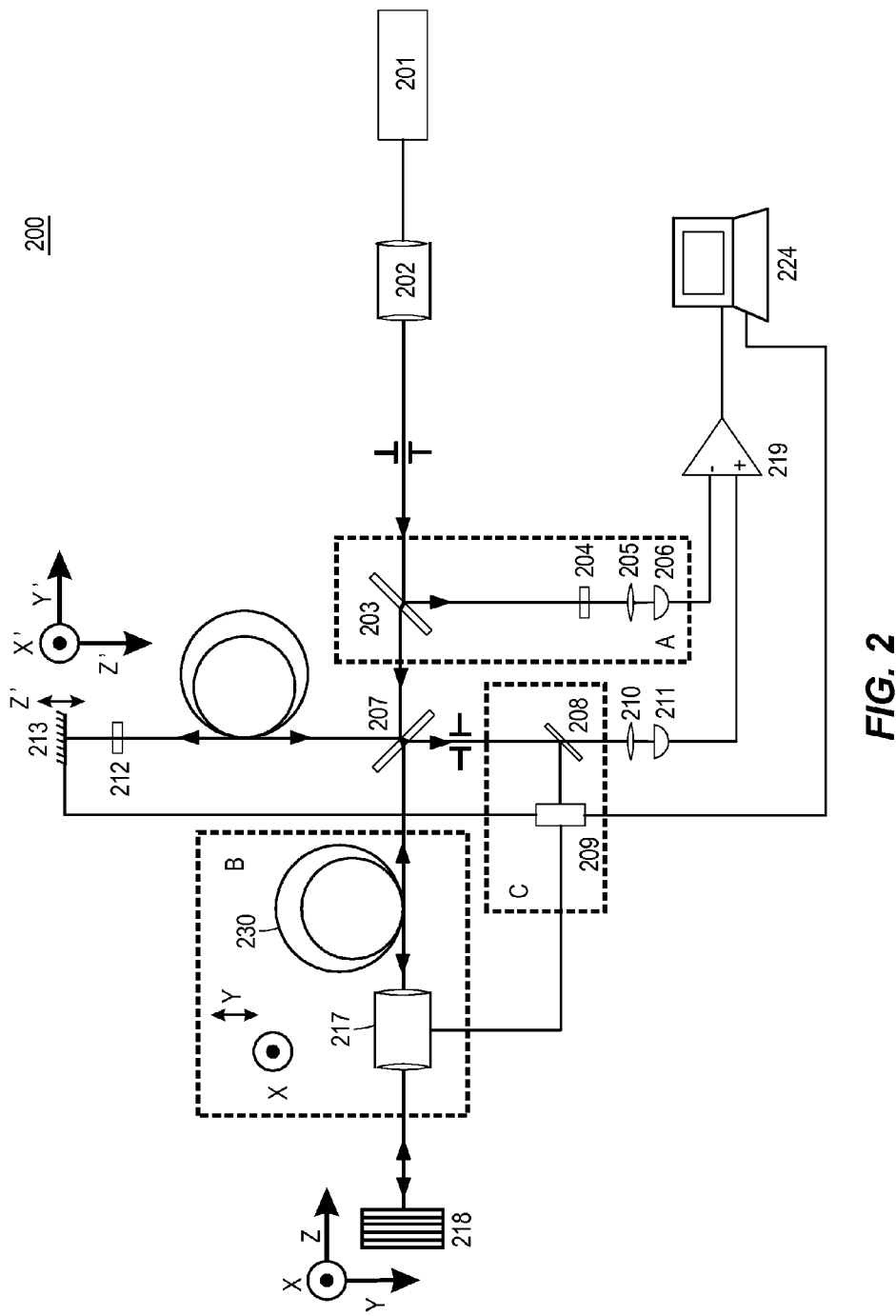
FIG. 2 illustrates a multi-layer transparent composite detection system, in accordance with another example.

FIG. 2 illustrates an example system 200, having like elements bearing similar reference numerals to those of FIG. 1, but in a 200 series set of numbers instead of a 100 series. The system 200 has a similar balanced photodetector stage A and beam tracking and alignment stage C similar to that of system 100. In the system 200, the scanning stage B is implemented with a flexible optical fiber 230 that delivers radiation from the main beamsplitter 207 to the adjustable optical telescope 217 and to the specimen 218, thus replacing the mirrors 114, 115, and 116 of the system 100. The fiber 230 also collects back-scattered radiation and reflected radiation from the specimen 218 and couples that radiation back to the main beamsplitter 207. Scanning in the XY-plane is achieved by adjusting the objective 217 along the x-axis and y-axis. In order to compensate for the optical path length in the specimen arm, a similar optical fiber 232 is used in the reference arm (between the main beamsplitter 207 and reference mirror 213). A tunable filter 212 is also used.

Use of optical fibers in the beam paths can provide stronger beam confinement and therefore better overlap of the interference beams. This results in increased resolution and signal intensity at the processor machine 224. The optical fibers can be single-mode optical fibers or multi-mode optical fibers. The optical fibers can be continuous core optical fibers, while in other examples, the optical fibers can have embedded features such fiber amplification regions and gradient based fiber resonating regions.

The techniques can be used to detect defects in multi-layer composites in any number of applications, including, by way of example, personal protection equipment, civil applications like security glass windows in banks and airports or defense applications such as transparent armor (TA) for military vehicles as well as for aircraft windshields.

Many other examples can be drawn from the automotive, aerospace, marine, and civil sectors. Each of these applications can involve different types of composite layers, different layer thicknesses, and different numbers of composite layers. Indeed the adaptability of the present techniques to be used for defect detection with various different composites, without system modification, is another attractive benefit.

The techniques may be integrated with manufacturing and field inspection, not just completed design.

We now describe a number of example implementations of the present techniques on different types of defects in a multi-layer transparent composite specimen. In these examples, two cases of defects were examined inside a transparent composite (TC) formed with polycarbonate or Corning® glass plates bonded together with Dureflex® A4700 transparent adhesive. The defects included a) delaminations (i.e., air gaps) between the layers and b) adhesive defects (i.e., air voids). The first defect, involving air gaps, was examined through two sets of experiments, one evaluating thin glass TCs and another evaluating thick glass TCs. For the thin glass TCs, each layer was approximate 1 mm thick, while approximately 12.6 mm layers were used for the thick glass TCs. Two types of laser sources were used, one a 639 nm diode laser from Toptica Photonics (iBeam-640s) operating at 60 mW power and whose temporal coherence gave a spatial resolution of approximate 0.07 mm, the other a 780 nm compact fiber laser, the FemtoFErb, also from Toptica Photonics, which gave a spatial resolution of approximately 0.03 mm. These proof of concept experiments were performed using a most basic configuration like that of system 100 that implemented a manually operated version of the beam tracking and alignment stage C and did not include optical telescopes 102 and 117, balanced photodetector stage A, of scanning stage B.

Figure 3:
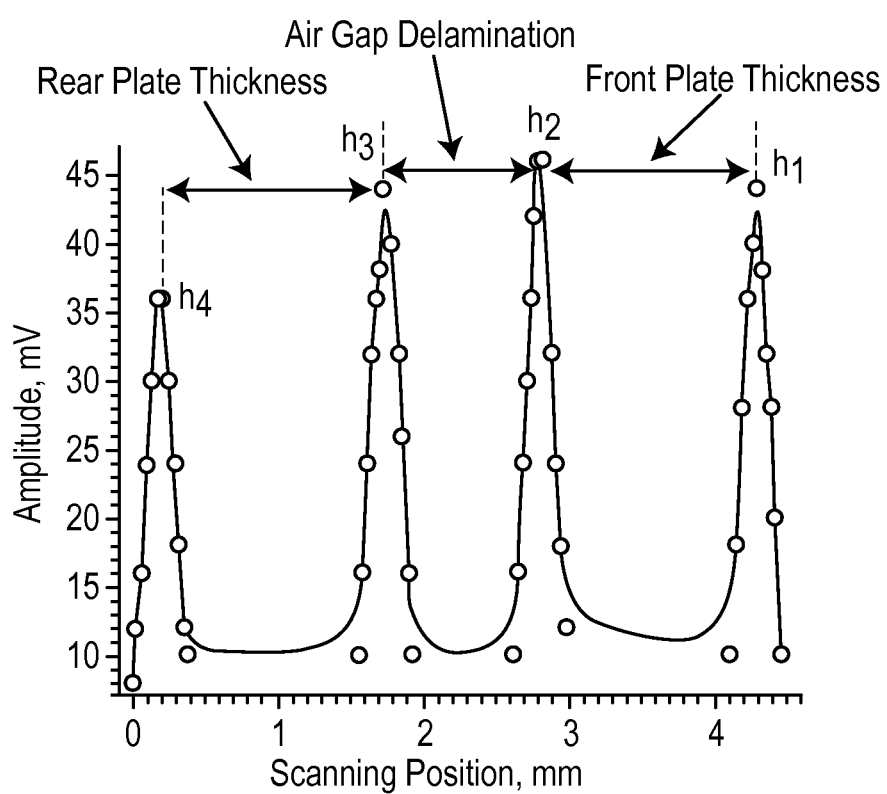
FIG. 3 is a plot of a signal amplitude dependence on the scanning position in the presence of delamination, in an example.

FIG. 3 illustrates the dependence of interference signal amplitude on the scanning position for an example delamination defect. The scanning position along the Z-axis is shown, in mm, as is the amplitude of the reflected signal measured by a photodetector, in mV, of the interference signal returned from various features in the specimen. At various scanning depths, signal spikes result from interference between one component of the reflected object beam and the reference beam. These spikes are identified in the figure as $h_1$, $h_2$, $h_3$, and $h_4$, with $h_1$ corresponding to interference with the portion of the beam reflected by the top surface of the front plate, nearest the objective lens. The front plate has a thickness determined from examining the spacing between the first reflection peak $h_1$ and the second reflection peak $h_2$. An air gap or delamination is shown extending between the second peak $h_2$ and the third peak $h_3$. Observe that the air gap is smaller than the thickness of the front plate, but still considerably large, large enough to present a major defect.

The processing system, which had the configuration of the system 124 (an oscilloscope), was able to determine the thickness of the layers (e.g., plates) and gaps from the peak positions. Every peak represents a reflection of radiation from an interface between material layers. Therefore, with the peak position and the refractive index of the material known, the processing system could straightforwardly determine the thickness of the layers or the air gap between the layers using the following formula:

$$h_{ik} = \frac{|h_i - h_k|}{n}, \quad (1)$$

Where $h_{ik}$ is the thickness of the layer or gap, $h_i$ and $h_k$ are adjacent peak positions and n is the refractive index of the material in a layer or air gap. In the illustration of FIG. 3, the peak positions are: $h_1$=4.3 mm, $h_2$=2.8 mm, $h_3$=1.73 mm, and $h_4$=0.19 mm. The refractive index of the Corning® glass (front and back layers) at wavelength 639 nm is 1.50798. Therefore, using Equation (1), the plate thickness and the delamination size was calculated. The front plate thickness, defined as the distance $h_1h_2$ was 0.99 mm, the rear plate thickness $h_3h_4$ was 1.02 mm and the delamination size $h_2h_3$ was 1.07 mm. These values were compared to those measured by digital calipers which provided the following values: a front plate thickness of 0.98 mm, a rear plate thickness of 1.05 mm, and a delamination size of 1.1 mm. A summary of the results in this case of delamination between parallel layers is presented in Table 1 below.

TABLE 1

Results summary for thin corning glass TC in case of delamination between parallel layers

|  | Values calculated using interference technique, mm | Values measured with digital calipers, mm | Difference in Measurements, mm/% |
| --- | --- | --- | --- |
| Front plate thickness | 0.99 ± 0.07 | 0.98 ± 0.05 | 0.01/1 |
| Rear plate thickness | 1.02 ± 0.07 | 1.05 ± 0.05 | 0.03/3 |
| Delamination size | 1.07 ± 0.07 | 1.10 ± 0.05 | 0.03/3 |

Figure 4:
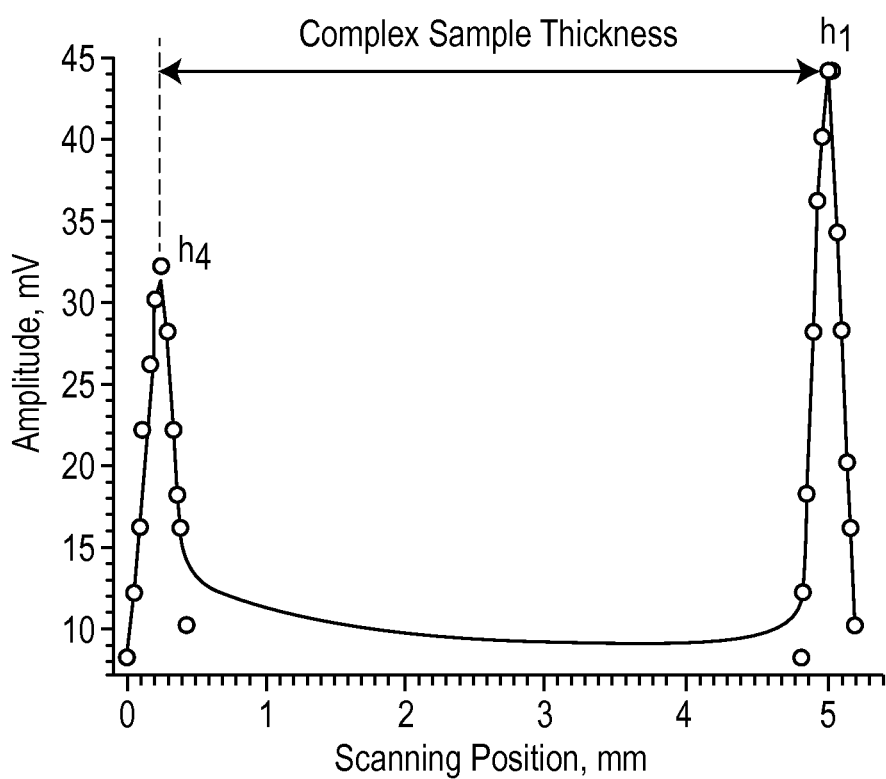
FIG. 4 is a plot of a signal amplitude dependence on the scanning position in the absence of delamination, in an example.

FIG. 4 illustrates the dependence of interference signal on the scanning position in the case of absence of delamination. As one can see, if delaminations are absent, there are no intense peaks related to an adhesive/glass interface. Only peaks related to the air/first plate front boundary and the rear plate back/air back boundary are present. That is, the signal peaks at $h_1$ and $h_4$, respectively, are shown, but no other peaks exist because no air gap/delamination defect is present. In this way, a processing system can develop and store interference signal patterns to look for when scanning a specimen. The processor system may identify a "normal" data pattern like that of FIG. 4, in comparison to that of FIG. 3, and automatically determine the presence of a delamination defect in the multi-layer transparent composite, and determine where the delamination defect occurs.

In order to calculate the reflection coefficients for s-polarized ($R_s$) and p-polarized ($R_p$) light at the interface between the materials, the Fresnel equations are used:

$$R_s = \left| \frac{n_1 \cos\theta_i - n_2\sqrt{1 - \left(\frac{n_1}{n_2}\sin\theta_1\right)^2}}{n_1 \cos\theta_i - n_2\sqrt{1 - \left(\frac{n_1}{n_2}\sin\theta_1\right)^2}} \right|^2, \quad (2)$$

$$R_p = \left| \frac{n_1 \sqrt{1 - \left(\frac{n_1}{n_2}\sin\theta_1\right)^2} - n_2\cos\theta_i}{n_1 \sqrt{1 - \left(\frac{n_1}{n_2}\sin\theta_1\right)^2} + n_2\cos\theta_i} \right|^2, \quad (3)$$

where $\theta_i$ is the angle of incidence, $n_1$ is the refractive index of the material where the light is reflected and $n_2$ is the refractive index of material where the light is further transmitted. In the case of normal incidence ($\theta_i$=0) these equations are simplified to the following formula:

$$R_s = R_p = \left|\frac{n_1 - n_2}{n_1 + n_2}\right|^2. \tag{4}$$

Using Equation (4), the calculated reflection coefficient for the air/glass interface was determined to be approximately 0.041. For the transparent adhesive (Dureflex® A4700), n=1.545, so the reflection coefficient for the glass/adhesive interface was determined to be approximately $1.47 \cdot 40^{-4}$. This meant that the amplitude of the signal reflected from the adhesive/glass interface was approximately 280 times weaker than the signal reflected from the air/glass interface and can be ignored in the current setup.

Figure 5:
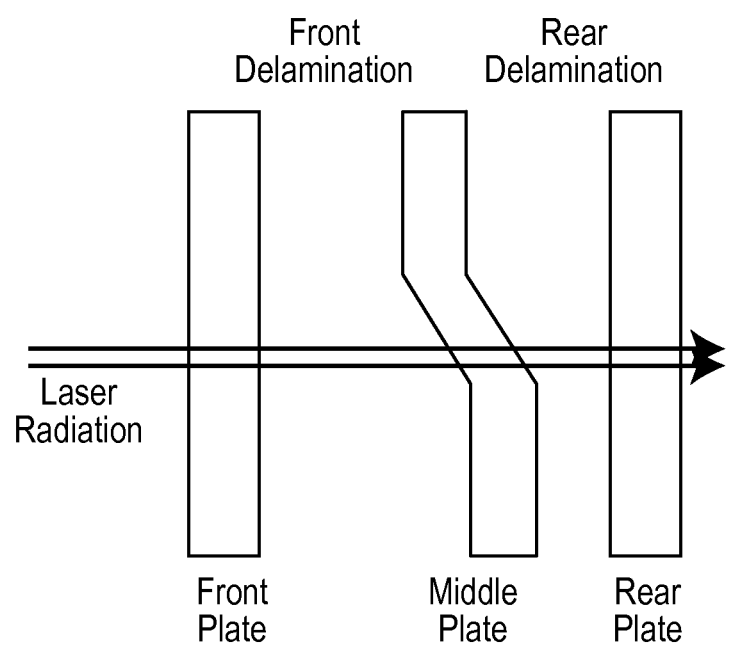
FIG. 5 is a schematic of a three-layer thin polycarbonate glass transparent composite with delamination between inclined plates, in an example.

In another example, the present technique was applied to a three-layer TC specimen formed of three thin layers (each with a layer thickness of approximately 1.5 mm) of polycarbonate glass plates bonded together with Dureflex® A4700 transparent adhesive. The sample had a delamination (air gap) between inclined glass plates (see FIG. 5). The light source used for inspection was the iBeam-640s laser described above.

Figure 6:
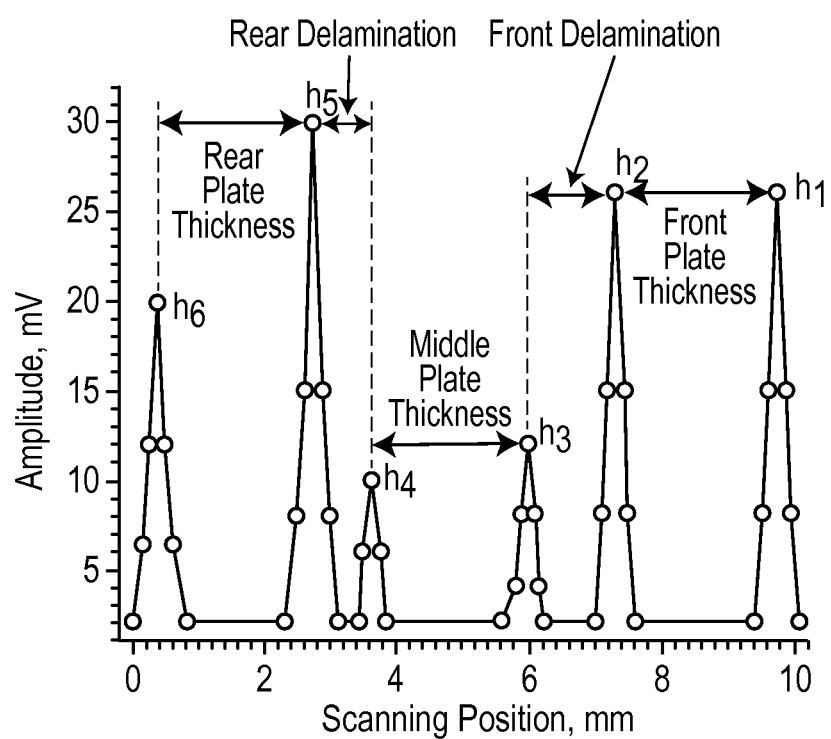
FIG. 6 is a plot of signal amplitude dependence on the scanning position for delamination between inclined layers, in accordance with an example.

The dependence of signal amplitude on the scanning position in this case of delamination between inclined layers and light from the iBeam-640s laser is shown in FIG. 6. The peak positions were: $h_1$=9.74 mm, $h_2$=7.3 mm, $h_3$=5.98 mm, $h_4$=3.62 mm, $h_5$=2.73 mm, $h_6$=0.39 mm. The refractive index of polycarbonate glass at 639 nm is 1.57964. Using Equation (1), the plates' thicknesses and the delamination sizes were determined. The plate thickness and delamination values calculated were compared to the values measured with digital calipers. A summary of the results from this evaluation of TC with delaminations between inclined layers through use of the iBeam-640s laser radiation is presented in Table 2.

TABLE 2

Results summary for thin PC glass TC in case of delamination between inclined layers, iBeam-640s laser radiation.

|  | Values calculated using interference technique, mm | Values measured with digital calipers, mm | Difference in Measurements, mm/% |
|---|---|---|---|
| Front plate thickness | 1.55 ± 0.07 | 1.59 ± 0.05 | 0.04/3 |
| Middle plate thickness | 1.49 ± 0.07 | 1.56 ± 0.05 | 0.07/4 |
| Rear plate thickness | 1.41 ± 0.07 | 1.53 ± 0.05 | 0.12/8 |
| Front delamination size | 1.32 ± 0.07 | 1.30 ± 0.05 | 0.02/2 |
| Rear delamination size | 0.89 ± 0.07 | 0.90 ± 0.05 | 0.01/1 |

Three additional sets of experiments were performed, applying the present techniques and using a laser source with a smaller spatial resolution, in particular the FemtoFErb 780 laser described above.

Figure 7:
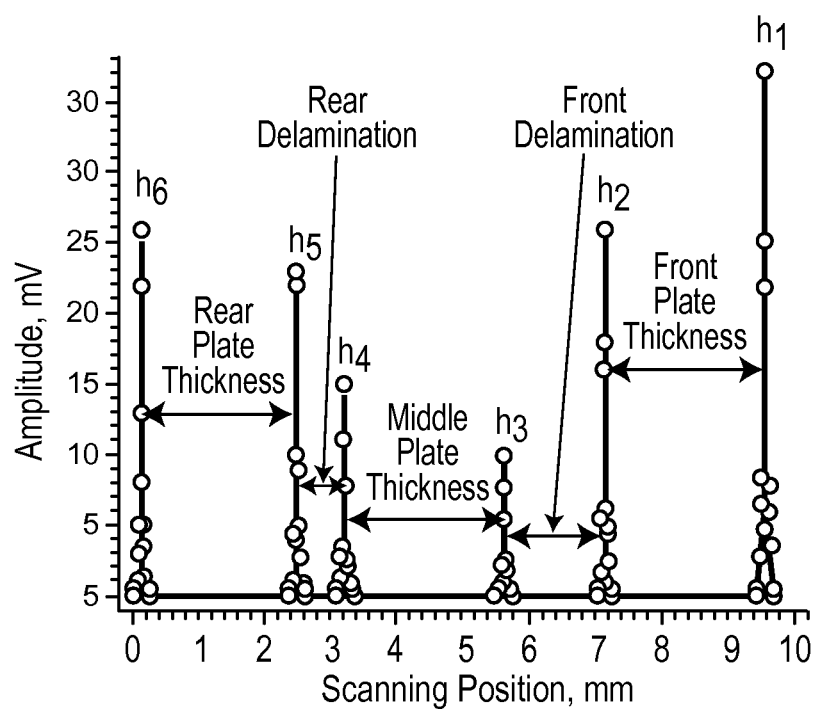
FIG. 7 is a plot of signal amplitude dependence on the scanning position for delamination between inclined layers, in accordance with another example using a different illumination laser source than that of FIG. 6.

In the first set of additional experiments, a three-layer TC with delaminations between thin (layer thickness approximately 1.5 mm) inclined polycarbonate glass plates was examined, the same specimen examined above. However, in order to achieve higher precision, the radiation from a FemtoFErb 780 laser with better (approximately 0.03 mm) spatial resolution was used. The dependence of signal amplitude on the scanning position for the TC sample with delamination between inclined layers and the FemtoFErb 780 laser as the light source is shown in FIG. 7. It must be noted that owing to the dependence of the delamination size on the in-plane (XY) scanning position, the results shown in FIG. 7 are similar but not exactly identical to those of FIG. 6. In this case of delamination between inclined layers the peak positions are: $h_1$=9.44 mm, $h_2$=7.04 mm, $h_3$=5.53 mm, $h_4$=3.16 mm, $h_5$=2.45 mm, $h_6$=0.14 mm. Using Equation (1) with n=1.57122, the plates' thicknesses and the delamination sizes were determined.

The values of plate thicknesses and delamination sizes from the experiment were compared to the values measured with digital calipers. The results are shown in Table 3.

TABLE 3

Results Summary for thin PC glass TC in case of delamination between inclined layers, FemtoFErb 780 laser radiation

|  | Values calculated using interference technique, mm | Values measured with digital calipers, mm | Difference in Measurements, mm/% |
|---|---|---|---|
| Front plate thickness | 1.55 ± 0.07 | 1.59 ± 0.05 | 0.04/3 |
| Middle plate thickness | 1.51 ± 0.03 | 1.56 ± 0.05 | 0.05/3 |
| Rear plate thickness | 1.49 ± 0.07 | 1.56 ± 0.05 | 0.07/4 |
| Front delamination size | 1.32 ± 0.07 | 1.30 ± 0.05 | 0.02/2 |
| Rear delamination size | 0.89 ± 0.07 | 0.90 ± 0.05 | 0.01/1 |

Figure 8:
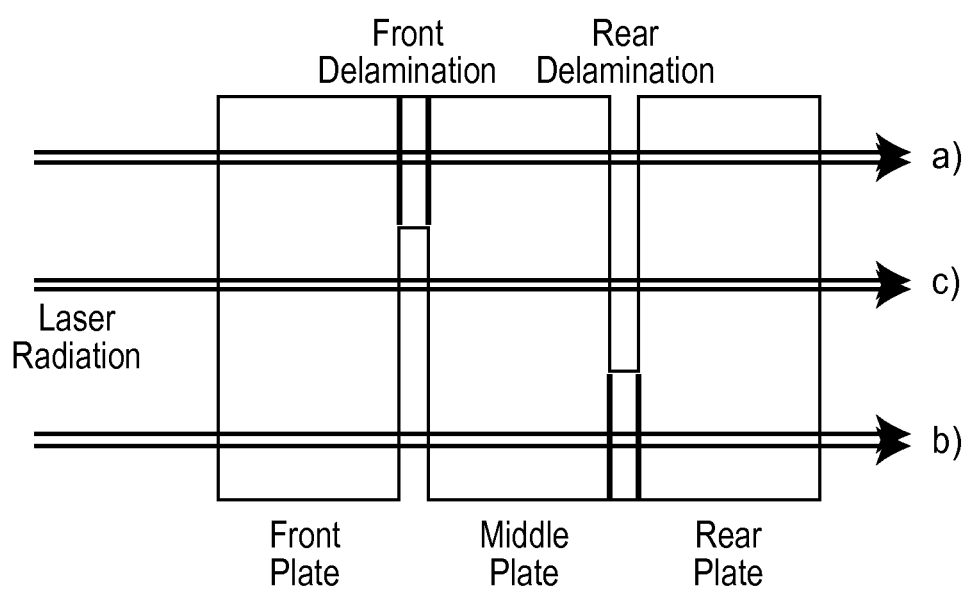
FIG. 8 is a schematic of a three-layer thick polycarbonate glass transparent composite sample with various locations of delaminations: a) rear delamination, b) front delamination, c) front and rear delaminations, in an example.
Figure 9:
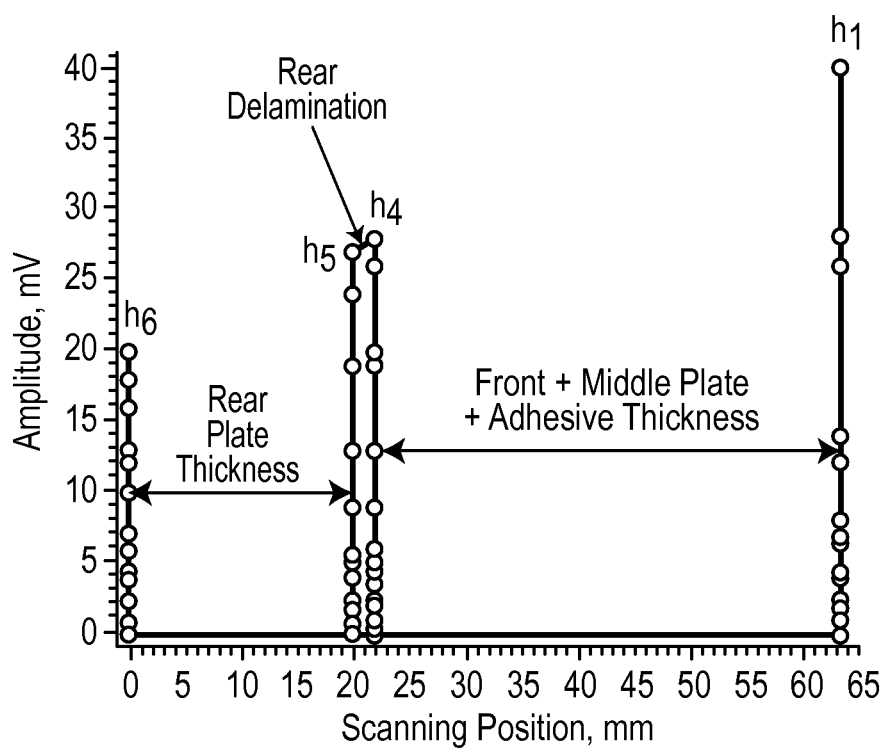
FIG. 9 is a plot of signal amplitude dependence on the scanning position for a transparent composite with rear delamination, in an example.

In the second set of these added experiments, a three-layer thick (layer thickness approximately 12.6 mm) polycarbonate glass TC with various locations of delaminations was examined. A schematic of the sample is shown in FIG. 8. Several cases of delamination location were studied. In the first case, the specimen has a delamination between the middle and the rear polycarbonate plates while the front and the middle PC plates are bonded with Dureflex® A4700 transparent adhesive (see FIG. 8, beam a). FIG. 9 illustrates the resulting plot of interference signal amplitude versus scanning position, showing peak positions at $h_1$=63.34 mm, $h_4$=22.07 mm, $h_5$=20.18 mm, and $h_6$=0.12 mm.

Figure 10:
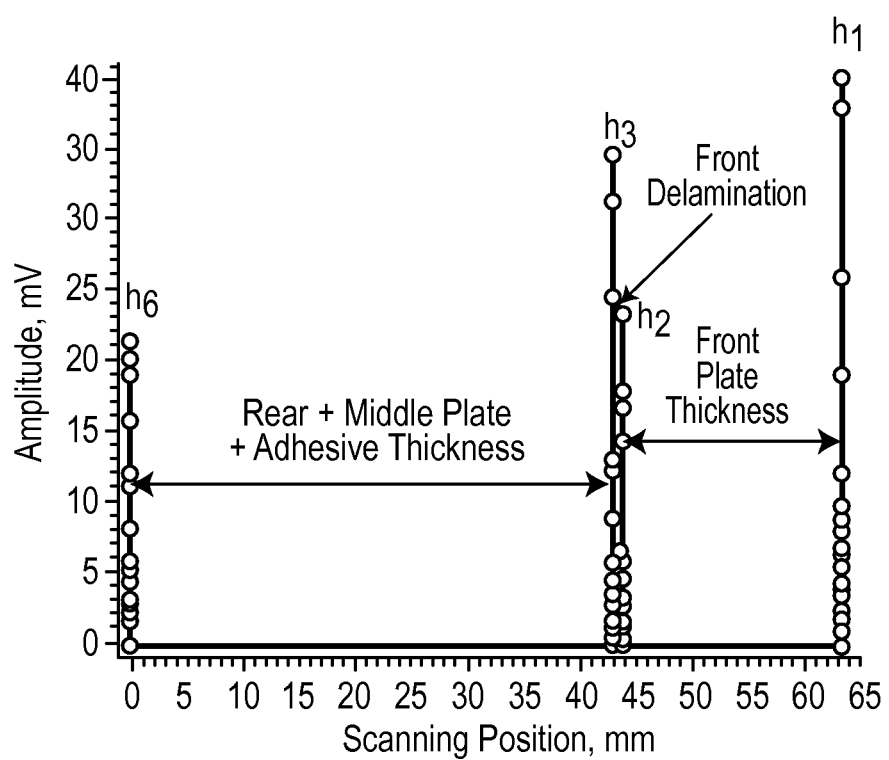
FIG. 10 is a plot of signal amplitude dependence on the scanning position for a transparent composite with front delamination, in an example.

In the second case, the specimen has a front delamination between the front and the middle polycarbonate plates while the middle and the rear polycarbonate plates were bonded with Dureflex® A4700 transparent adhesive (see FIG. 8, beam b). FIG. 10 illustrates the resulting plot of interference signal amplitude versus scanning position, showing peak positions at $h_1$=63.74 mm, $h_2$=43.71 mm, $h_3$=40.9 mm, and $h_6$=0.12 mm.

Figure 11:
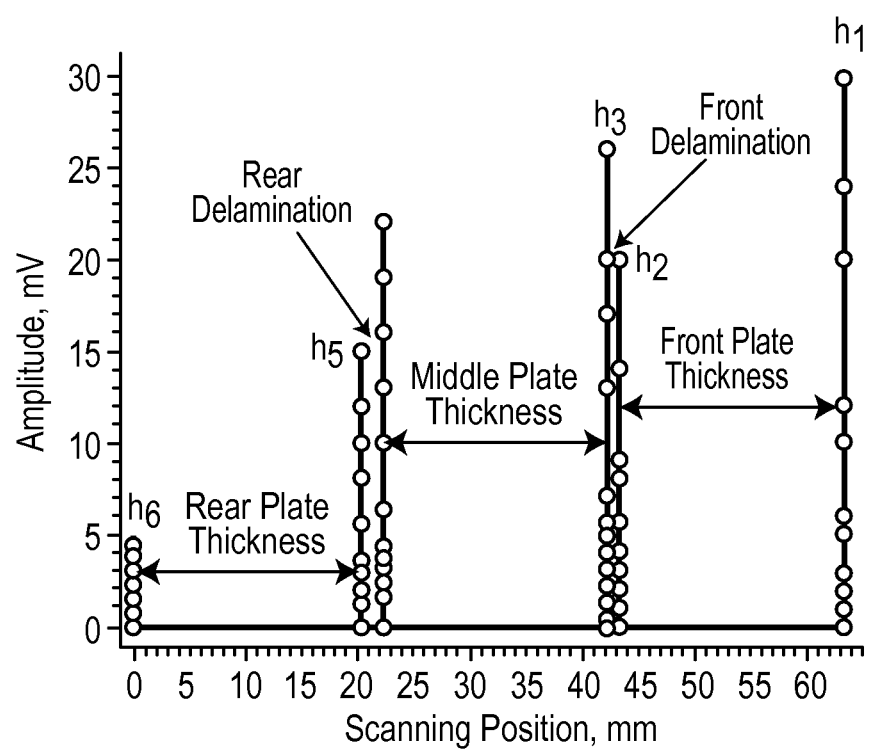
FIG. 11 is a plot of signal amplitude dependence on the scanning position for a thick transparent composite with multiple delaminations, in an example.

In the third case, the TC has multiple delaminations, one each between the front and middle and the middle and rear PC plates (see FIG. 8, beam c). FIG. 11 illustrates the resulting plot of interference signal amplitude versus scanning position, showing peak positions at $h_1$=63.13 mm, $h_2$=43.01 mm, $h_3$=42.07 mm, $h_4$=22.16 mm, $h_5$=20.23 mm, $h_6$=0.11 mm.

Figure 12:
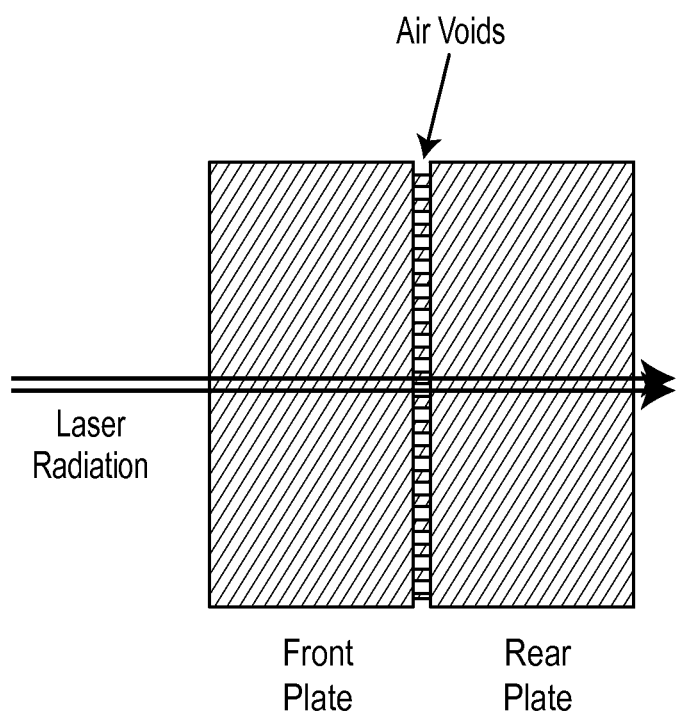
FIG. 12 is an example schematic of a two-layer thick polycarbonate glass transparent composite sample with adhesive defect (air voids), in an example.
Figure 13:
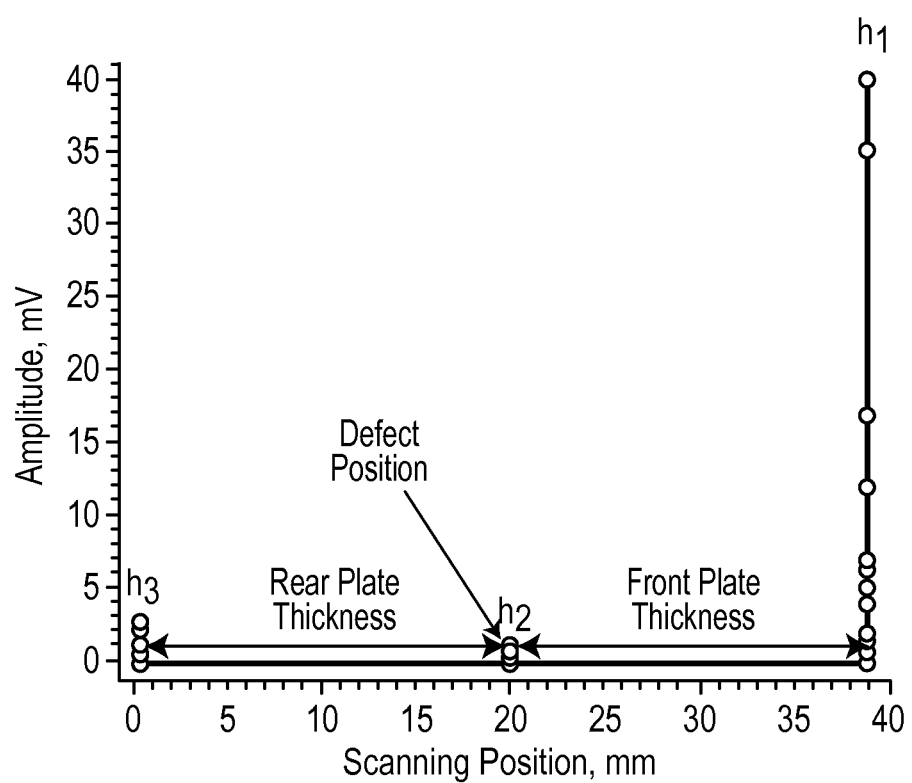
FIG. 13 is a plot of signal amplitude dependence on the scanning position for a transparent composite having an adhesive defect (air voids), in an example.

Another set of experiments were performed to detect adhesive defects in the form of air voids. FIG. 12 illustrates a schematic of the sample and FIG. 13 illustrates the results of the interference signal, showing peak positions at $h_1$=38.82 mm, $h_2$=19.75 mm, and $h_3$=0.12 mm.

Another application of the present techniques is in the measurement of induced displacements, induced relative displacements, and, hence, induced strains in the interior of three-dimensional (3D) objects made of transparent or semi-transparent materials. The challenge of interior strain measurement has not been properly addressed with conventional techniques. Existing techniques require embedding strain gages or gratings to obtain only the displacements of one plane, that or some have proposed placing a layer of speckle material in the composite for digital image correlation.

In reference to the system 100, movement of the reference beam mirror 113 can be precisely known throughout its full range of motion. In some examples, the coarse adjustment capability of the mirror 113 is eliminated (or stopped) and only calibrated fine adjustments are used. The system 100 then is used to measure the distance between layers, between other already in-place features such as bubbles or particles, or between particles or other features deliberately incorporated into the structure for the purposes of relative displacement and strain measurement. These features serve as fiducial markers, and the distance between them is called the gage length. The measurement is performed on the specimen in its initial state. The specimen is then deformed as by the application of mechanical loads or by a temperature change, and such deformation changes the distance between these fiducial markers. This new distance is then measured. The first measurement is subtracted from the second measurement to give the change of gage length. The change of gage length is then divided by the original gage length to find the average normal strain, which is an important value in engineering design.

This technique yields the transverse strain, that is, the strain in the through-thickness direction. If the specimen itself is also mounted on a translation stage, or other suitable structure, the technique can be used to obtain precise measurements of motion in the in-plane X and Y directions, as well, and then the procedure will yield normal strains in these directions. Thus, all three components of normal strain become known, meaning the complete state of strain is known for the region that has been examined.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A method of scanning a multi-layered specimen, the method comprising:
    receiving a coherent radiation beam and separating the coherent radiation beam into an object beam and a reference beam, the object beam and the reference beam being coherent with one another;
    directing the object beam at the specimen and collecting a resulting sampled beam from the specimen, wherein the sampled beam comprises reflected radiation from the specimen and/or backscattered radiation from the specimen;
    maintaining the reference beam along a reference beam path and free from incidence on the specimen, and scanning the reference beam along different optical path lengths of the reference beam path, wherein the scanning of the reference beam is along a reference axis coinciding with an axis into the specimen and over a depth region into the specimen;
    combining the sampled beam with the reference beam to produce an interferometric intensity signal or pattern, where, as a result of the scanning of the reference beam, the interferometric pattern contains amplitude peaks that are caused by reflection or scattering from discontinuities at different depths within the depth region of the specimen;
    identifying, in a signal processing machine, the depth positions, within the specimen, of each of the discontinuities from the positions of the amplitude peaks in the interferometric pattern, wherein the discontinuities represent fiducial markers within the specimen;
    determining, in the signal processing machine, a distance between at least two of the fiducial markers;
    deforming the specimen in at least one direction;
    identifying, in the signal processing machine, updated depth positions, within the specimen, of the at least two fiducial markers; and
    determining, in the signal processing machine, an updated distance between the at least two fiducial markers.

2. The method of claim 1, the method further comprising:
    identifying, in the signal processing machine, a layer within the multi-layer specimen that corresponds to the each of the discontinuities.

3. The method of claim 1, wherein the discontinuities are an air gap in the multi-layer specimen or a delamination defect in the multi-layer specimen.

4. The method of claim 1, the method further comprising:
    scanning the object beam across a two-dimensional area of the specimen to collect the sampled beam over the two-dimensional area;
    identifying the discontinuities in the multi-layered specimen, in response to the scanning of the object beam and the scanning of the reference beam; and
    determining a three-dimensional position of each of the identified discontinuities and determining a three-dimensional size of each of the identified discontinuities.

5. The method of claim 1, wherein scanning the reference beam along the different optical path lengths of the reference beam path comprises:
    providing a coarse-increment level scanning of the reference beam to allow for larger scans along the reference axis and a fine-increment level scanning of the reference beam for smaller scans along the reference axis.

6. The method of claim 5, the method further comprising:
    automatically selecting between coarse-increment level scanning and fine-increment level scanning based on changes in the interferometric pattern.

7. The method of claim 1, the method further comprising:
    forming a signal balancing beam from the coherent radiation beam; and
    performing noise signal balancing on the interferometric pattern using the signal balancing beam.

8. The method of claim 1, wherein a coherence length of the coherent radiation beam is between 1 micrometer and 1 millimeter.

9. The method of claim 1, the method further comprising:
    determining a change in gage length for the multi-layered specimen from the distance and the updated distance; and
    determining strain, in the at least one direction, for the multi-layered specimen.

10. The method of claim 1, the method further comprising:
    deforming the multi-layered specimen in a plurality of directions;
    determining a change in gage length for the multi-layered specimen from the distance and the updated distance and for each of the plurality of directions; and
    determining strain, in each of the plurality of directions, for the multi-layered specimen.

11. An apparatus for scanning a multi-layered specimen, the apparatus comprising:
    a beam splitter positioned to receive a coherent radiation beam and configured to separate the coherent radiation beam into an object beam and a reference beam, the object beam and the reference beam being coherent with one another;
    a specimen scanning stage configured to direct the object beam at the specimen and collect a resulting sampled beam from the specimen, wherein the sampled beam comprises reflected radiation from the specimen and/or backscattered radiation from the specimen;

a reference beam stage having a scanning mirror and configured (i) to maintain the reference beam along a reference beam path and free from incidence on the specimen and (ii) to scan the reference beam along different optical path lengths of the reference beam path, wherein the scanning of the reference beam is along a reference axis coinciding with an axis into the specimen and over a depth region into the specimen; and a signal processing machine configured to, in response to combining the sampled beam with the reference beam and producing an interferometric pattern, where, as a result of the scanning of the reference beam, the interferometric pattern contains amplitude peaks corresponding to discontinuities at different depths within the depth region of the specimen, and (ii) to (i) analyze the interferometric pattern to identify discontinuities in the specimen from the peaks in the interferometric pattern, (ii) identify the depth positions, within the specimen, of each of the discontinuities from the positions of the amplitude peaks in the interferometric pattern, wherein the discontinuities represent fiducial markers within the specimen, (iii) determine a distance between at least two of the fiducial markers;

(iv) in response to deforming the specimen in at least one direction, identify updated depth positions, within the specimen, of the at least two fiducial markers; and (v) determine an updated distance between the at least two fiducial markers.

12. The apparatus of claim 11, wherein the signal processing machine is configured to identify a layer within the multi-layer specimen that corresponds to the each of the discontinuities.

13. The apparatus of claim 11, wherein the discontinuities are an air gap in the multi-layer specimen or a delamination defect in the multi-layer specimen.

14. The apparatus of claim 11, wherein the specimen scanning stage comprises an X-axis scanning element and a Y-axis scanning element to scan the object beam across a two-dimensional area of the specimen to collect the sampled beam over the two-dimensional area.

15. The apparatus of claim 14, wherein the signal processing machine is configured to (i) identify the discontinuities in the multi-layered specimen, in response to the scanning of the object beam and the scanning of the reference beam, (ii) determine a three-dimensional position of each of the identified discontinuities, and (iii) determine a three-dimensional size of each of the identified discontinuities.

16. The apparatus of claim 11, the apparatus further comprising:
the scanning mirror in the reference beam path; and
a beam tracking and alignment stage that implements angular alignment and motion of the scanning mirror using (i) a coarse-increment level scanning of the reference beam to allow for larger scans along the reference axis and (ii) a fine-increment level scanning of the reference beam for smaller scans along the reference axis.

17. The apparatus of claim 16, wherein the beam tracking and alignment stage comprises a beam monitoring device coupled to monitor at least a portion of combined reference beam and object beam to establish coincidence of the reference beam and the object beam, wherein the beam tracking and alignment stage is coupled to the signal processing machine and configured to selectively move between coarse-increment level scanning and fine-increment level scanning in response to control from the signal processing machine.

18. The apparatus of claim 11, the apparatus further comprising:
a signal balancing stage coupled to form a signal balancing beam from the coherent radiation beam, wherein the signal processing machine is configured to perform noise signal balancing on the interferometric pattern using the signal balancing beam.

19. The apparatus of claim 11, wherein the signal processing machine is further configured to:
(vi) determine a change in gage length for the specimen from the distance and the updated distance; and
(vii) determine strain, in the at least one direction, for the specimen.

* * * * *

UNITED STATES PATENT AND TRADEMARK OFFICE
CERTIFICATE OF CORRECTION

| | | |
|---|---|---|
| PATENT NO. | : 9,500,468 B2 | Page 1 of 1 |
| APPLICATION NO. | : 14/833843 | |
| DATED | : November 22, 2016 | |
| INVENTOR(S) | : Anton S. Khomenko et al. | |

It is certified that error appears in the above-identified patent and that said Letters Patent is hereby corrected as shown below:

In the Claims

At Column 15, Line 18, "specimen, and (ii) to" should be -- specimen, --.

At Column 15, Line 28, "markers;" should be -- markers, --.

At Column 15, Line 31, "markers; and" should be -- markers, and --.

Signed and Sealed this
Fourth Day of July, 2017

Joseph Matal
*Performing the Functions and Duties of the
Under Secretary of Commerce for Intellectual Property and
Director of the United States Patent and Trademark Office*